US006372237B1

United States Patent
Boussouira et al.

(10) Patent No.: US 6,372,237 B1
(45) Date of Patent: *Apr. 16, 2002

(54) COMPOSITION COMPRISING A CINNAMIC ACID DERIVATIVE AND A POLYAMINO POLYMER

(75) Inventors: Boudiaf Boussouira, Paris; Didier Candau, Bievres, both of (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/703,930

(22) Filed: Nov. 2, 2000

Related U.S. Application Data

(63) Continuation of application No. 09/083,029, filed on May 22, 1998, now Pat. No. 6,180,119.

(30) Foreign Application Priority Data

May 28, 1997 (FR) .............................................. 97 06532

(51) Int. Cl.$^7$ ................................................. A61K 6/00
(52) U.S. Cl. ........................... 424/401; 424/59; 424/60; 424/70.17; 424/70.15; 424/70.16
(58) Field of Search ............................ 424/401, 59, 60, 424/70.17, 70.15, 70.16, 641, 642; 514/944, 945

(56) References Cited

U.S. PATENT DOCUMENTS

| | | | |
|---|---|---|---|
| 4,144,123 A | 3/1979 | Scharf et al. ................ 162/164 |
| 4,360,646 A | 11/1982 | Denkewalter et al. ....... 525/420 |
| 4,631,337 A | 12/1986 | Tomalia et al. .............. 528/391 |
| 4,694,064 A | 9/1987 | Tomalia et al. .............. 528/332 |
| 5,204,099 A | 4/1993 | Barbier et al. ............... 424/401 |
| 5,384,115 A | 1/1995 | Bissett et al. ................. 424/59 |
| 5,425,938 A | 6/1995 | Znaiden et al. ........... 424/78.02 |
| 5,449,519 A | 9/1995 | Wolf et al. .................. 424/401 |
| 5,556,616 A | 9/1996 | Janchitraponvej et al. ....... 424/70.12 |
| 5,618,521 A | * 4/1997 | de Rigal et al. ............... 424/59 |
| 5,733,895 A | 3/1998 | Forestier ....................... 514/63 |
| 5,776,440 A | * 7/1998 | Forrestier et al. ............. 424/59 |
| 5,904,735 A | 5/1999 | Gutirrez et al. ................. 8/137 |
| 5,910,513 A | 6/1999 | Galey ......................... 514/649 |

FOREIGN PATENT DOCUMENTS

| | | |
|---|---|---|
| DE | 3 743 744 | 7/1989 |
| EP | 0 114 607 | 8/1984 |
| EP | 0 487 404 | 5/1992 |
| EP | 0 518 772 | 12/1992 |
| EP | 0 518 773 | 12/1992 |
| EP | 0 541 018 | 5/1993 |
| EP | 0 590 538 | 4/1994 |
| EP | 0 682 059 | 11/1995 |
| EP | 0 684 044 | 11/1995 |
| EP | 0 782 846 | 7/1997 |
| FR | 1 477 147 | 4/1967 |
| FR | 2 315 991 | 1/1977 |
| FR | 2 326 405 | 4/1977 |
| FR | 2 416 008 | 8/1979 |
| FR | 2 440 933 | 6/1980 |
| FR | 2 658 076 | 8/1991 |
| FR | 0 816 324 | 1/1998 |
| JP | 69007395 | 2/1969 |
| JP | 3-183620 | 8/1991 |
| WO | WO 90/09777 | 9/1990 |
| WO | WO 93/04665 | 3/1993 |
| WO | WO 93/04666 | 3/1993 |
| WO | WO 93/14147 | 7/1993 |
| WO | WO 94/12560 | 6/1994 |
| WO | WO 94/14873 | 7/1994 |
| WO | WO 94/20681 | 9/1994 |
| WO | WO 94/29422 | 12/1994 |
| WO | WO 95/02008 | 1/1995 |
| WO | WO 96/12754 | 5/1996 |
| WO | WO 96/14345 | 5/1996 |
| WO | WO 96/14346 | 5/1996 |
| WO | WO 96/29080 | 9/1996 |
| WO | WO 97/14404 | 4/1997 |

OTHER PUBLICATIONS

Nicole Ardoin et al., "Molecular trees: from syntheses towards applications", Bull. Soc. Cim. Fr. (1995) 132, 875–909.

A.D. Bangham et al., "Diffusion of Univalent Ions across the lamellae of Swollen Phospholipids", J. Mol. Biol. (1965) 13, 238–252.

D.H. Davies et al., "Copolymerization of Acrylic Acid with 1–Substituted Imidazoles", Macromolecules, vol. 6, No. 2, Mar.–Apr. 1973, pp. 163–168.

Craig J. Hawker et al., Preparation of Polymers with Controlled Molecular Architecture. A New Convergent Approach to Dendritic Macromolecules, J. Am. Chem. Soc. 1990, 112, 7638–7647.

Kirk–Othmer, Encyclopendia of Chemical Technology, Third Edition, vol. 20, pp. 214–216.

Harold N. Feigenbaum, "Polyethylenimine: Prospective Applications", Cosmetics & Toiletries, vol. 108, Aug. 1993, pp. 73–77.

C.G. Overberger et al., "Esterolytic Activities of Copolymers Containing Imidazole Groups", Annals of the New York Academy of Sciences, vol. 155, Art. 2, Jan. 27, 1969, pp. 431–446.

(List continued on next page.)

*Primary Examiner*—Thurman K. Page
*Assistant Examiner*—Lakshmi Channavajjala
(74) *Attorney, Agent, or Firm*—Finnegan Henderson Farabow Garrett & Dunner, L.L.P.

(57) ABSTRACT

Novel cosmetic and/or dermatological compositions comprising, in a cosmetically and/or dermatologically acceptable vehicle, i) a cinnamic acid derivative, in particular 2-ethylhexyl p-methoxycinnamate, and ii) at least one polyamino polymer, and the use of these compositions in the cosmetic and/or dermatological fields. These compositions are particularly photostable.

38 Claims, No Drawings

OTHER PUBLICATIONS

C.G. Overberger et al., "Imidazole–containing Polymers. Synthesis and Polymerization of the Monomer 4(5)–Vinylimidazole", Journal of the American Chemical Society, vol. 85, No. 7, Apr. 5, 1963, pp. 951–955.

"Synthesis and Polymerization of 2–Vinylimidazole and 2–Vinylbenzimidazole", Polymer Letters Edition, John Wiley & Sons, Inc., vol. 11 (1973), pp. 465–469.

Mitchell L. Schlossman, "Treated Pigments, New Ways to Impart Color on the Skin", Cosmetics & Toiletries, vol. 105, Feb. 1990, pp. 53–64.

James P. Tam, "Synthetic peptide vaccine design: Synthesis and properties of a high–density multiple antigenic peptide system", Proc. Natl. Acad. Sci, vol. 85, Aug. 1988, pp. 5409–5413.

Jiro Tanaka, "Copolymerization Behavior of N–Vinylimidazole with Various Dialkyl maleates and Fumarates", J. Macromol. Sci.–Chem, A21(2), (1984), pp. 253–265.

Donald A. Tomalia, "Starburst Demdrimers: Molecular –Level Control Size, Shape, Surface Chemistry, Topology, and Flexibility from Atoms to Macroscopic Matter", Angewandte Chemie, vol. 29, No. 2, Feb. 1990, pp. 138–175.

B.I. Voit, "Dendritic polymers: from aesthetic macromolecules to commercially interesting materials", Acta Polymer., 46, (1995), pp. 87–99.

* cited by examiner

COMPOSITION COMPRISING A CINNAMIC ACID DERIVATIVE AND A POLYAMINO POLYMER

This application is a continuation of U.S. application Ser. No. 09/083,029, filed May 22, 1998, now U.S. Pat. No. 6,180,119.

Applicants reference herein the patent applications of BOUDIAF BOUSSOUIRA and DIDIER CANDAU for COMPOSITION COMPRISING A DIBENZOYL-METHANE DERIVATIVE AND A POLYAMINO POLYMER (Docket No. 05725.0304), and of BOUDIAF BOUSSOUIRA and CHRISTIAN COLIN for COSMETIC USE OF SELECTED POLYAMINO POLYMERS AS ANTIOXIDANTS (Docket No. 05257.0306), filed on even date herewith and incorporate the disclosures thereof specifically by reference herein.

The present invention relates to novel cosmetic and/or dermatological compositions (hereinafter known as anti-sun compositions) intended for the protection of the skin and/or hair against UV radiation, in particular solar radiation. More specifically, it relates to novel cosmetic and/or dermatological compositions exhibiting an improved photostability and comprising, in a cosmetically and/or dermatologically acceptable vehicle, the combination of two specific compounds.

The invention also relates to the use of these compositions in the cosmetic and/or dermatological fields.

It is known that light radiation with wavelengths ranging from 280 nm to 400 nm makes it possible for the human skin to brown and that radiation with wavelengths more particularly from 280 to 320 nm, known under the name of UV-B, cause erythemas and skin burns which can harm the development of natural tanning. For these reasons and for aesthetic reasons, there exists a continual demand for means for controlling this natural tanning, for the purpose of thus controlling the colour of the skin; it is thus advisable to screen out this UV-B radiation.

It is also known that UV-A radiation, with wavelengths ranging from 320 to 400 nm, which causes the skin to brown, are capable of leading to a detrimental change in the latter, in particular in the case of sensitive skin or skin which is continually exposed to solar radiation. In particular, UV-A radiation causes a loss of skin elasticity and the appearance of wrinkles, leading to premature skin ageing. It promotes the triggering of the erythemal reaction or accentuates this reaction in certain subjects and can even be the cause of phototoxic or photoallergic reactions. Thus, for aesthetic and cosmetic reasons, such as preservation of the natural elasticity of the skin, for example, more and more people wish to control the effect of UV-A radiation on their skin. It is thus desirable to screen out the UV-A radiation as well.

Thus, with the aim of providing protection of the skin and hair against all UV-A radiation which is as complete and as efficient as possible, use is generally made, in the manufacture of anti-sun compositions, of combinations of screening agents active in the UV-A and of screening agents active in the UV-B.

In this respect, a particularly advantageous family of UV-B screening agents is currently composed of cinnamic acid derivatives, and in particular 2-ethylhexyl p-methoxycinnamate, because these compounds exhibit a high intrinsic absorption power. In addition, other cinnamic acid derivatives have highly advantageous properties in cosmetics, such as, for example, caffeic acid, which is well known as a depigmenting agent.

Now, some cinnamic acid derivatives exhibit the disadvantage of chemically degrading under certain conditions, in particular when they are exposed to UV radiation. When they are subjected to such degradation, these active principles, derived from cinnamic acid, lose their potential for activity.

Use is frequently made, in anti-UV compositions, of tocopherol derivatives, which are known for their properties in combating free radicals and which contribute, via these properties, to retaining the youthfulness of the skin.

However, the inventors have found that cinnamic acid derivatives, in particular 2-ethylhexyl p-methoxycinnamate, when they are in the presence of tocopherol derivatives and under UV irradiation, chemically degrade to a significant extent. Under these conditions, the combination of the two compounds no longer allows prolonged broad anti-sun protection of the skin and hair.

Such a degradation reaction is particularly significant when the cinnamic acid derivative is used in combination with another organic screening agent, in particular screening agents of the dibenzoylmethane family, which are anti-UV-A screening agents. In particular, the combination of cinnamic acid derivatives with 4-tert-butyl-4'- methoxydibenzoylmethane is highly advantageous. These screening agents are very often used in combination in skin and hair products because their spectra of activity are complementary.

Now, following significant research carried out in the field of the photoprotection mentioned above, the inventors have now discovered that the introduction of certain polyamino polymers, which will be defined more specifically hereinbelow, into a composition containing a cinnamic acid derivative, in particular 2-ethylhexyl p-methoxycinnamate, made it possible to improve, in an entirely remarkable way, the photostability of this compound within such compositions and thus the overall efficiency of these compositions.

A subject-matter of the present invention is thus novel cosmetic and/or dermatological compositions comprising, in a cosmetically and/or dermatologically acceptable vehicle:

a) at least one cinnamic acid derivative corresponding to the following formula (I):

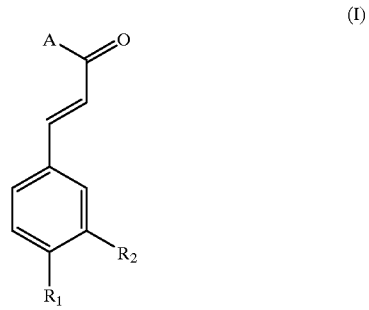

in which:

A represents:

an $OR_3$ radical, $R_3$ being selected from: a hydrogen atom, a phytyl or benzyl radical, a saturated or unsaturated, linear, branched or cyclic, $C_1$–$C_{18}$ alkyl chain, an alkali or alkaline earth metal ion or an ammonium ion, or an $NHR_4$ radical, $R_4$ being selected from: a hydrogen atom, a phytyl or benzyl radical or a saturated or unsaturated, linear, branched or cyclic, $C_1$–$C_{18}$ alkyl chain;

$R_1$ represents a radical selected from: H, OH, $C_1$–$C_6$ alkoxy, preferably methoxy, or a saturated or unsaturated, linear, branched or cyclic, $C_1$–$C_{18}$ alkyl chain;

$R_2$ represents a radical selected from: H, OH or $C_1$–$C_6$ alkoxy, preferably methoxy, and b) at least one polyamino polymer selected from the following families:

(A) a polyalkylene polyamine selected from:
(i) polyalkylene polyamines;
(ii) alkylated derivatives of polyalkylene polyamines;
(iii) addition products of alkylcarboxylic acids with polyalkylene polyamines;
(iv) addition products of ketones and aldehydes with polyalkylene polyamines;
(v) addition products of isocyanates and isothiocyanates with polyalkylene polyamines;
(vi) addition products of alkylene oxide and poly(alkylene oxide) block polymers with polyalkylene polyamines;
(vii) quaternized derivatives of polyalkylene polyamines;
(viii) addition products of a silicone with polyalkylene polyamines;
(ix) copolymers of dicarboxylic acid and polyalkylene polyamines;
(B) polyvinylimidazoles;
(C) polyvinylpyridines;
(D) addition products of 1-vinylimidazole monomers of formula (1):

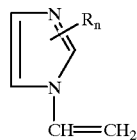

(I)

in which the R radical independently represents H or a saturated or unsaturated, linear or cyclic, $C_1$–$C_6$ alkyl radical;
n is an integer ranging from 1 to 3, with the polyalkylene polyamines (A)(i) to (A)(ix);
(E) polymers based on amino acids containing a basic side chain;
(F) crosslinked derivatives of the polymers (A)(i) to (A)(ix), (B), (C), (D) and (E).

Another subject-matter of the invention is novel cosmetic and/or dermatological compositions comprising, in a cosmetically and/or dermatologically acceptable vehicle:
a) at least one cinnamic acid derivative corresponding to the formula (I) defined hereinabove;
b) at least one polyamino polymer as defined hereinabove; and
c) at least one derivative corresponding to the formula (II):

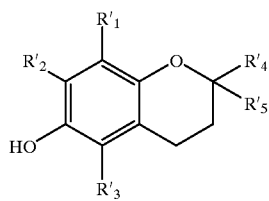

(II)

in which:
$R'_1$, $R'_2$ and $R'_3$ independently represent a radical selected from: H, OH or $C_1$–$C_6$ alkyl, preferably methyl,
$R'_4$ represents a radical selected from: H or $C_1$–$C_6$ alkyl, preferably methyl, $R'_5$ represents a radical selected from: H or $C_1$–$C_{18}$ alkyl, among which mention may in particular be made of tocopherol derivatives.

An additional subject-matter of the invention is novel cosmetic and/or dermatological compositions comprising, in a cosmetically and/or dermatologically acceptable vehicle:
a) at least one cinnamic acid derivative corresponding to the formula (I) defined hereinabove,
b) at least one polyamino polymer as defined hereinabove, and
d) at least one dibenzoylmethane derivative corresponding to the following formula (III):

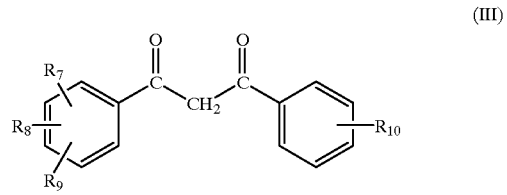

(III)

in which:
$R_7$, $R_8$, $R_9$ and $R_{10}$ independently represent hydrogen or a hydroxyl radical or a linear or branched $C_1$–$C_8$ alkyl radical or a linear or branched $C_1$–$C_8$ alkoxy radical.

Thus, according to the present invention, cosmetic and/or dermatological compositions can be prepared containing a cinnamic acid derivative, in particular 2-ethylhexyl p-methoxycinnamate, optionally in combination with at least one derivative of formula (II), in particular a tocopherol derivative, or at least one dibenzoylmethane derivative, in which compositions the concentration of cinnamic acid derivative remains relatively constant even if these compositions are subjected to the action of light.

A further subject-matter of the present invention is the use of a polyamino polymer in, or for the manufacture of, cosmetic and/or dermatological compositions containing a cinnamic acid derivative as defined above (formula (I)), in particular 2-ethylhexyl p-methoxycinnamate, optionally in combination with at least one derivative of formula (II) as defined above and/or in combination with at least one dibenzoylmethane derivative as defined above (formula (III)), with the aim of improving, in these compositions, the stability to UV radiation (photostability) of the cinnamic acid derivative.

Another subject-matter of the present invention is a process for improving the stability to UV radiation (photostability), and thus the efficiency, of a cosmetic and/or dermatological composition comprising a cinnamic acid derivative as defined above (formula (I)), in particular 2-ethylhexyl p-methoxycinnamate, and optionally a derivative of formula (II) as defined above and/or a dibenzoylmethane derivative as defined above (formula (III)), this process consisting in introducing, into the composition, an effective amount of a polyamino polymer.

Effective amount of polyamino polymer is understood to mean an amount sufficient to obtain a noteworthy and significant improvement in the photostability of the cinnamic acid derivative or derivatives contained in the composition. This minimum amount of stabilizing agent to be employed, which can vary according to the nature of the cosmetically acceptable vehicle used in the composition, can be determined without any difficulty by means of a conventional test for the measurement of photostability, such as that given in the examples shown below.

Other characteristics, aspects and advantages of the present invention will become apparent on reading the detailed description which will follow.

The polyamino polymers which can be used in the present invention can be in the linear polymer, hyperbranched polymer or dendrimer form.

Hyperbranched polymers are molecular constructions having a branched structure, generally around a core. Their structure is generally devoid of symmetry: the base units or monomers which have been used in the construction of the hyperbranched polymer can be different in nature and their distribution is irregular. The branches of the polymer can be different in nature and in length. The number of base units, or monomers, can be different depending on the different branching. While being asymmetric, hyperbranched polymers can have: an extremely branched structure, around a core; successive layers or generations of branching; a layer of terminal chains.

Hyperbranched polymers generally result from the polycondensation of one or more monomers ABx, A and B being reactive groups capable of reacting together and x being an integer greater than or equal to 2, but other preparation processes can be envisaged. Hyperbranched polymers are characterized by their degree of polymerization DP=1-b, b being the percentage of non-terminal functionalities in B which have not reacted with a group A. As the condensation is non-systematic, in contrast to the synthesis of dendrimers, the degree of polymerization is less than 100%. Usually, by known synthetic methods, DP is between 15 and 90%. A terminal group T on the hyperbranched polymer can be made to react in order to obtain a specific functionality at the chain end.

Such polymers are described in particular in B. I. Voit, Acta Polymer., 46, 87–99 (1995); EP-682,059; WO-9614346; WO-9614345; WO-9612754, the disclosures of which are specifically incorporated by reference herein.

Several hyperbranched polymers can be combined with one another, via a covalent bond or another type of bond, by means of their terminal groups. Such so-called bridged polymers come within the definition of hyperbranched polymers according to the present invention.

Dendrimers are highly branched polymers and oligomers, which are also known, having a well defined chemical structure and they are said to be "perfect" hyperbranched polymers. As a general rule, dendrimers comprise a core, a defined number of generations of branches, or spindles, and terminal groups. The generations of spindles are composed of structural units which are identical for the same generation of spindles and which can be identical or different for different generations of spindles. The generations of spindles extend radially in a geometrical progression from the core. The terminal groups of a dendrimer of the Nth generation are the terminal functional groups of the spindles of the Nth generation or terminal generation. Such polymers are described in particular in D. A. Tomalia, A. M. Naylor and W. A. Goddard III, *Angewandte Chemie*, Int. Ed. Engl. 29, 138–175 (1990); C. J. Hawker and J. M. J. Frechet, J. Am. Chem. Soc., 112, 7638 (1990); B. I. Voit, Acta Polymer., 46, 87–99 (1995); N. Ardoin and D. Astruc, Bull. Soc. Chim. Fr., 132, 875–909 (1995), the disclosures of which are specifically incorporated by reference herein.

Dendrimers can also be defined more particularly by the following formula (DI):

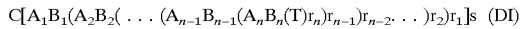

C[A$_1$B$_1$(A$_2$B$_2$( . . . (A$_{n-1}$B$_{n-1}$(A$_n$B$_n$(T)r$_n$)r$_{n-1}$)r$_{n-2}$. . . )r$_2$)r$_1$]s (DI)

in which:

C represents the core, connected via a number s of functionalities to s spindles A$_1$B$_1$ via groups A$_1$;

s is an integer greater than or equal to 1 and less than or equal to the number of functionalities in C;

the index i (i=1, 2 . . . n) is an integer which denotes the generation of each spindle;

r$_i$(i=1, 2 . . . n−1) represents the number of functionalities in the group B$_i$ belonging to the spindle (A$_i$B$_i$), r$_i$ being an integer greater than or equal to 2;

for each spindle (A$_i$B$_i$) (i=1, 2 . . . n), the group B$_i$ is connected to r$_i$ groups A$_{i+1}$ of a spindle (A$_{i+1}$B$_{i+1}$);

each group A$_i$ (i≧2) is connected to only one group B$_{i-1}$ of the spindle (A$_{i-1}$B$_{i-1}$);

the spindle of nth generation A$_n$B$_n$ is chemically bonded to a number r$_n$ of terminal groups T, r$_n$ being an integer greater than or equal to zero.

The definition of dendrimers given above includes molecules with symmetrical branching; it also includes molecules with non-symmetrical branching, such as, for example, dendrimers in which the spindles are lysine groups, in which the branching of one generation of spindles on the preceding generation takes place on the α and ε amines of the lysine, which results in a difference in the length of the spindles for the different branching.

Dense star polymers, starburst polymers and rod-shaped dendrimers are included in the present definition of dendrimers. The molecules known as arborols and cascade molecules also come within the definition of dendrimers according to the present invention.

Several dendrimers can be combined with one another via a covalent bond or another type of bond, by means of their terminal groups, to give entities known under the name of "bridged dendrimers". Such entities are included in the definition of dendrimers according to the present invention.

Dendrimers can exist in the form of an assembly of molecules of the same generation, which are so-called monodisperse assemblies; they can also exist in the form of assemblies of different generations, which are so-called polydisperse assemblies. The definition of dendrimers according to the present invention includes both monodisperse and polydisperse assemblies of dendrimers.

Reference may be made to the following documents, in which are described dendrimers containing amine functional groups, the contents of these documents being incorporated by reference in the present description: U.S. Pat. No. 4,694, 064; U.S. Pat. No. 4,631,337; WO-A-9502008; WO-A-9314147; U.S. Pat. No. 4,360,646; Proc. Natl. Acad. Sci. USA, 85, 5409–5413 (1988), the disclosures of which are specifically incorporated by reference herein.

Hyperbranched polymers and dendrimers containing amino functional groups can also be composed of a core and of generations of base units, monomers or spindles, of any nature, on which a terminal group T carrying an amine functional group has been grafted.

The polyamino polymers (A)(i) to (A)(ix), (B), (C), (D), (E) and (F) of the invention will be described in greater detail:

(A) (I) the polyalkylene polyamines preferably used according to the invention are polymers containing from 7 to 20,000 repeat units. The choice is preferably made of polyalkylene polyamines comprising at least 5% of tertiary amines, advantageously at least 10% of tertiary amine functional groups and more preferably still at least 20%. These polymers can be homopolymers or copolymers which are linear, branched or of dendrimer structure.

These polymers comprise the following repeat units:

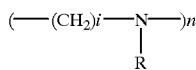

in which:
i represents an integer greater than or equal to 2, preferably i=2;
n represents an integer
R represents H or a unit

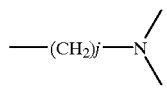

in which j represents an integer greater than or equal to 2, preferably j=2;

Among the products of the family of polyalkylene polyamines, also known as polyaziridines, mention may in particular be made of:
polyethyleneimine, which is a hyperbranched polymer well known to a person skilled in the art: on the subject of polyethyleneimine, reference may be made in particular to the documents: "Kirk-Othmer Encyclopedia of Chemical Technology", 3rd edition, Vol. 20, 1982, p. 214–216 and "Polyethyleneimine Prospective Application", H. N. Feigenbaum, Cosmetic & Toiletries, 108, 1993, p. 73, the disclosures of which are specifically incorporated by reference herein. Polyethyleneimine is available commercially from the company BASF under the trade names LUPASOL and POLYIMIN; polyethyleneimine is usually within an average molecular weight range from 500 to 2,000,000.

Polyethyleneimines and polypropyleneimines in the form of dendrimers, manufactured by the company DSM, are also known. Patent Applications WO 95/02008 and WO 93/14147, the disclosures of which are specifically incorporated by reference herein, describe polyalkylene polyamines of the family of the dendrimers and a process for their preparation.

(A)(ii) alkylated derivatives of polyalkylene polyamines are products well known to a person skilled in the art. They are obtained in a known way by alkylation, in aqueous or alcoholic medium, in the presence of an alkylating agent, preferably in the presence of NaOH, of KOH or of carbonate, at temperatures preferably ranging from 40° C. to 130° C. The alkylating agent can be selected, for example, from $C_1$–$C_8$ alkyl halide or alkyl sulphate derivatives, such as, for example, dimethyl sulphate, diethyl sulphate, butyl bromide, hexyl bromide, 2-ethylhexyl bromide, n-octyl bromide or the corresponding chlorides. Reference may be made, for example, to DE-3,743,744, which describes the preparation of such products and the contents of which are incorporated by reference in the contents of the present application.

(A)(iii) addition products of alkylcarboxylic acids with polyalkylene polyamines are products known to a person skilled in the art, the preparation of which is described, for example, in Patent Applications WO 94/14873; WO 94/20681 and WO 94/12560, the disclosures of which are specifically incorporated by reference herein. The addition of alkylcarboxylic acids to polyalkylene polyamines can be carried out by reacting, in a known way, an acid, an amide, an ester or an acid halide with the polyalkylene polyamine polymer.

Addition products of alkylcarboxylic acids with polyalkyleneamines can be, for example, the addition products of saturated or unsaturated, linear or branched, $C_2$–$C_{30}$ alkylcarboxylic acids with a polyethyleneimine. Mention may be made, among the carboxylic acids which can be used, of, for example, acetic acid, propionic acid, butyric acid, 2-ethylhexanoic acid, benzoic acid, lauric acid, myristic acid, palmitic acid, stearic acid, oleic acid, linoleic acid, arachidonic acid or behenic acid, and mixtures of fatty substances, such as, for example, mixtures of fatty esters available in the form of natural products and among which may be mentioned: coconut oil, soybean oil, linseed oil or rapeseed oil.

(A)(iv) addition products of ketones and aldehydes with polyalkylene polyamines (A)(i) can be prepared by processes known to a person skilled in the art and result in α-hydroxyamine units being obtained;

(A)(v) addition products of isocyanates and isothiocyanates with polyalkylene polyamines (A)(i) can be prepared by processes known to a person skilled in the art and result in urea and thiourea units being obtained;

(A)(vi) addition products of alkylene oxide and poly (alkylene oxide) block polymers with polyalkylene polyamines (A)(i) can be prepared by processes known to a person skilled in the art; reference may be made, for example, to the documents EP-541,018 and U.S. Pat. No. 4,144,123, the disclosures of which are specifically incorporated by reference herein, in which such molecules are described; ethoxylated polyethyleneimine derivatives are available commercially under the trade name: LUPASOL 61 (BASF)

(A)(vii) quaternized derivatives of polyalkylene polyamines (A)(i) can be prepared by processes known to a person skilled in the art;

(A)(viii) addition products of a silicone with polyalkylene polyamines (A)(i) are, for example, polyethyleneimines grafted by polydimethylsiloxane units, the preparation of which is described in the document U.S. Pat. No. 5,556,616, the disclosure of which is specifically incorporated by reference herein, which are sold by the company MacIntyre under the trade name MACKAMER PAVS;

(A)(ix) copolymers of dicarboxylic acid and polyalkylene polyamines (A)(i) can be prepared by polycondensation of dicarboxylic acids with polyalkylene polyamines.

Mention may be made, among dicarboxylic acids which can be used for the preparation of the polyamidoamines, of $C_2$ to $C_{10}$ dicarboxylic acids, such as, for example, oxalic acid, malonic acid, itaconic acid, succinic acid, maleic acid, adipic acid, glutaric acid, sebacic acid, terephthalic acid or orthophthalic acid, and their mixtures.

The polyalkylene polyamines used for the preparation of the polyamidoamines are advantageously selected from those having from 3 to 10 nitrogen atoms, such as, for example, diethylenetriamine, triethylenetetramine, dipropylenetriamine, tripropylenetetramine, dihexamethylenetriamine, aminopropylethylenediamine, bisaminopropylethylenediamine and their mixtures. Use may also be made of polyethyleneimines, such as described above, for the preparation of polyamidoamines.

Such compounds are described, for example, in documents: U.S. Pat. No. 4,144,423 and WO 94/29422, the disclosures of which are specifically incorporated by reference herein.

(B) the term polyvinylimidazole comprises the homopolymers and copolymers of polyvinylimidazole (PVI) obtained by radical polymerization of the vinylimidazole monomers with the following structure:

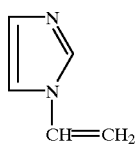

The copolymers can be, for example, copolymers of vinylimidazole containing at least 5% of vinylimidazole units with monomers selected from the units: vinylpyrrolidinone, acrylic acid and acrylamide. The synthesis of such compounds is well known to a person skilled in the art; in this respect, reference may in particular be made to the documents: J. Am. Chem. Soc., Vol. 85, 1962, p. 951; Polymer Letters Ed., Vol. 11, 1973, p. 465–469; Macromolecules, Vol. 6(2), 1973, p. 163–168; Ann. N. Y. Acad. Sci., Vol.155, 1969, p. 431; FR-A-1,477,147; JP-69 07395; J. Macromol. Scien. Chem., Vol. A21(2), 1984, p. 253, the disclosures of which are specifically incorporated by reference herein.

(C) the term polyvinylpyridine comprises the homopolymers and copolymers of vinylpyridine obtained by radical polymerization of the vinylpyridine monomers (substituted at the 2- or 4-position of the pyridine nucleus) with the following structure:

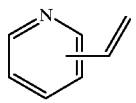

The copolymers can be, for example, copolymers of vinylpyridine containing at least 5% of vinylpyridine units with monomers selected from the units:
vinylpyrrolidinone, acrylic acid and acrylamide.

(D) addition products of 1-vinylimidazole monomers corresponding to the formula (I):

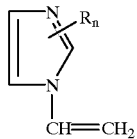

(I)

in which the R radicals independently represent H or a saturated or unsaturated, linear or cyclic, $C_1$–$C_6$ alkyl radical,
n is an integer ranging from 1 to 3, with the polyalkylene polyamines and their derivatives (A)(i) to (A)(ix).

Mention may be made, among the derivatives of formula (I) which can be used, of, for example, 2-methyl-1-vinylimidazole or 2-benzyl-1-vinylimidazole.

These products are known to a person skilled in the art: their preparation is described, for example, in Patent Application WO 94/29422, the disclosures of which are specifically incorporated by reference herein.

(E) polymers based on amino acids containing a basic side chain are preferably selected from proteins and peptides comprising at least 5%, advantageously at least 10%, of amino acids selected from histidine, lysine or arginine.

Mention may be made, among these polymers, of, for example, polylysines or polyhistidines.

(F) crosslinked derivatives of the polymers (A)(i) to (A)(ix), (B), (C) and (D). Mention may be made, among the crosslinking agents which can be used, of halohydrin-, glycidyl, aziridino- or isocyanate derivatives; such crosslinking agents and their methods of use are well known to a person skilled in the art. Mention may be made, among the most well known, of: epichlorohydrin, α,ω-bis(chlorohydrin)polyalkylene glycol ethers, or α,ω-dichloroalkanes, such as, for example, 1,2-dichloroethane, 1,2-dichloropropane, 1,3-dichloropropane, 1,4-dichlorobutane and 1,6-dichlorohexane; such crosslinking agents and their use in crosslinking polyethyleneimine derivatives are described in WO 94/12560, the disclosure of which is specifically incorporated by reference herein.

Preferably, polyamino polymers comprising at least 5% of tertiary amines, advantageously at least 10% of tertiary amine functional groups and more preferably still at least 20% are selected in the implementation of the present invention.

According to the invention, the polyamino polymer is advantageously selected from:

(A)(i) hyperbranched polyethyleneimines, (ii) alkylated polyethyleneimine derivatives;

(iii) addition products of alkylcarboxylic acids with polyethyleneimine;

(iv) addition products of ketones and aldehydes with polyethyleneimine;

(v) addition products of isocyanates and isothiocyanates with polyethyleneimine;

(vi) addition products of alkylene oxide and poly(alkylene oxide) block polymers with polyethyleneimine;

(vii) quaternized derivatives of polyethyleneimine;

(viii) addition products of a silicone with polyethyleneimine;

(ix) copolymers of dicarboxylic acid and of polyethyleneimine;

(B) polyvinylimidazoles.

More preferably still, the polyamino polymer is selected from:

(A) (i) hyperbranched polyethyleneimines. Preferably, polyethyleneimines comprising at least 5% of tertiary amines, advantageously of at least 10% of tertiary amine functional groups and more preferably still at least 20% are selected.

As indicated above, the cinnamic acid derivatives which can be used according to the present invention are those corresponding to the above formula (I).

According to the present invention, it is possible, of course, to employ one or more cinnamic acid derivatives.

Mention may in particular be made, among cinnamic acid derivatives which can be used according to the present invention, without implied limitation, of: 2-ethylhexyl p-methoxycinnamate, dihydroxycinnamic acid, also known as caffeic acid, chlorogenic acid and caffeoylquinic derivatives.

Preference is very particularly given, according to the present invention, among the cinnamic acid derivatives mentioned above, to the use of 2-ethylhexyl p-methoxycinnamate, this screening agent thus corresponding to the following expanded formula:

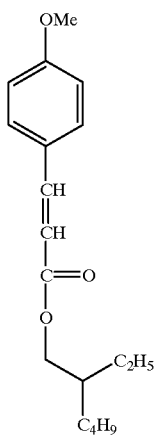

The cinnamic acid derivatives can be present in the compositions of the invention at a content preferably ranging from 0.1% to 10% by weight with respect to the total weight of the composition. This content more preferably ranges from 0.5% to 5%.

A second compound of the compositions according to the invention is a compound of the family of polyamino polymers.

Generally, the polyamino polymer or polymers can be present in the compositions in accordance with the invention at contents preferably ranging from 0.1% to 10% by weight and more preferably from 0.25% to 5% by weight, with respect to the total weight of the composition.

The polyamino polymer is preferably introduced into the compositions according to the invention in the neutralized form.

Thus, when a sufficient amount of a polyamino polymer is added to an anti-sun composition containing a cinnamic acid derivative, in particular 2-ethylhexyl p-methoxycinnamate, and a derivative of formula (II) as defined above, an increase in the stability of the said cinnamic acid derivative to light, and thus an improvement in the efficiency of the anti-sun composition over time, is observed.

The compound of formula (II) is advantageously tocopherol.

According to this preferred embodiment of the invention, the tocopherol is advantageously present in the composition in "the free state", that is to say without an additional group and in particular without an ester-forming group.

The tocopherol used is preferably a mixture of natural tocopherols, in particular of α-tocopherol, of β-tocopherol, of γ-tocopherol and of δ-tocopherol; this mixture can be used in particular in an oil selected from vegetable, mineral or silicone oils, and preferably vegetable oils.

Mention may be made, as mixture of natural tocopherols which can be used according to the invention, of that, as a 50% solution in soybean oil, sold by the Company Bizen under the name D MIXED TOCOPHEROLS. The D-α-tocopherol sold by the Company Henkel under the name COPHEROL F1300 or alternatively those described in the document U.S. Pat. No. 4,144,325, the disclosure of which is specifically incorporated by reference herein, can also be used.

The derivative or derivatives of formula (II) are generally present in the compositions of the invention at a content which can preferably range from 0.5% to 20%, more preferably from 1% to 10%, by weight with respect to the total weight of the composition.

The dibenzoylmethane derivatives correspond to the following formula (III):

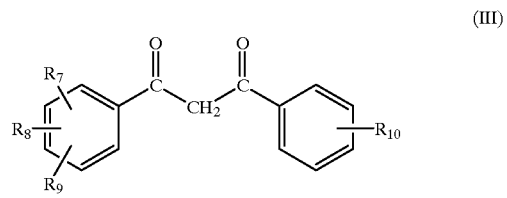

in which $R_7$, $R_8$, $R_9$ and $R_{10}$ independently represent hydrogen or a hydroxyl radical or a linear or branched $C_1$–$C_8$ alkyl radical or a linear or branched $C_1$–$C_8$ alkoxy radical.

Mention may in particular be made, among the dibenzoylmethane derivatives which can be used according to the present invention, of, without implied limitation:

2-methyldibenzoylmethane,
4-methyldibenzoylmethane,
4-isopropyldibenzoylmethane,
4-tert-butyldibenzoylmethane,
2,4-dimethyldibenzoylmethane,
2,5-dimethyldibenzoylmethane,
4,4'-diisopropyldibenzoylmethane,
4-tert-butyl-4'-methoxydibenzoylmethane,
2-methyl-5-isopropyl-4'-methoxydibenzoylmethane,
2-methyl-5-tert-butyl-4'-methoxydibenzoylmethane,
2,4-dimethyl-4'-methoxydibenzoylmethane,
2,6-dimethyl-4-tert-butyl-4'-methoxydibenzoylmethane,
4,4'-dimethoxydibenzoylmethane.

These products are already well known and are described in particular in the abovementioned documents FR-A-2,326,405, FR-A-2,440,933 and EP-A-0,114,607, the disclosures of which are specifically incorporated by reference herein.

Among the dibenzoylmethane derivatives mentioned above, it is very particularly preferred, according to the present invention, to employ 4-tert-butyl-4'-methoxydibenzoylmethane, this screening agent thus corresponding to the following expanded formula:

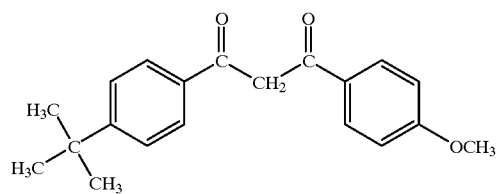

Another preferred dibenzoylmethane derivative according to the present invention is 4-isopropyldibenzoylmethane, a screening agent corresponding to the following expanded formula:

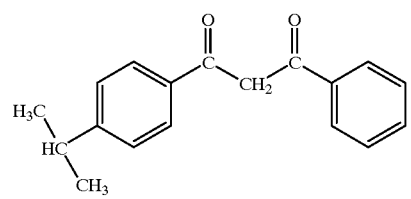

The dibenzoylmethane derivatives can be present in the compositions of the invention at a content preferably ranging from 0.2% to 15% by weight with respect to the total weight of the composition. This content more preferably ranges from 0.2% to 10%.

Thus, when a sufficient amount of a polyamino polymer is added to an anti-sun composition containing a dibenzoylmethane derivative, in particular 4-tert-butyl-4'-methoxydibenzoylmethane, a and a cinnamic acid derivative, an increase in the stability of the cinnamic acid derivative to light, and thus an improvement in the efficiency of the anti-sun composition over time, is observed.

The cosmetic and/or dermatological compositions targeted by the present invention can, of course, contain one or more additional, hydrophilic or lipophilic, sunscreens active in the UV-A and/or UV-B (absorbers), other, of course, than the screening agents mentioned above. These additional screening agents can be selected in particular from salicylic derivatives, benzylidenecamphor derivatives, benzimidazole derivatives, triazine derivatives, benzophenone derivatives, β,β'-diphenylacrylate derivatives, p-aminobenzoic acid derivatives, or the screening polymers and screening silicones described in Application WO 93/04665, the disclosure of which is specifically incorporated by reference herein. Other examples of organic screening agents are given in Patent Application EP-A-0,487,404, the disclosure of which is specifically incorporated by reference herein.

The compositions according to the invention can also contain agents for the artificial tanning and/or browning of the skin (self-tanning agents), such as, for example, dihydroxyacetone (DHA).

The cosmetic and/or dermatological compositions according to the invention can also contain pigments or else nanopigments (mean size of the primary particles: preferably from 5 nm and 100 nm, more preferably from 10 to 50, nm) of metal oxides which are coated or non-coated, such as, for example, titanium oxide (amorphous or crystallized in the rutile and/or anatase form), iron oxide, zinc oxide, zirconium oxide or cerium oxide nanopigments, which are all photoprotective agents well known per se which act by physically blocking (reflection and/or scattering) UV radiation. Conventional coating agents are, furthermore, alumina and/or aluminium stearate. Such coated or non-coated metal oxide nanopigments are described in particular in Patent Applications EP-A-0,518,772 and EP-A-0,518,773, the disclosures of which are specifically incorporated by reference herein.

The compositions in accordance with the present invention can comprise, in addition, conventional cosmetic adjuvants selected in particular from fatty substances, organic solvents, ionic or non-ionic thickeners, softeners, antioxidants, agents for combating free radicals, opacifying agents, stabilizers, emollients, silicones, α-hydroxy acids, antifoaming agents, moisturizing agents, vitamins, fragrances, preservatives, surfactants, fillers, sequestering agents, polymers, propellants, basifying or acidifying agents, dyes or any other ingredient commonly used in the cosmetic and/or dermatological field, in particular for the manufacture of anti-sun compositions in the form of emulsions.

The fatty substances can be composed of an oil or a wax or their mixtures. Oil is understood to mean a compound which is liquid at ambient temperature. Wax is understood to mean a compound which is solid or substantially solid at ambient temperature and with a melting point generally greater than 35° C.

Mention may be made, as oils, of mineral oils (liquid petrolatum); vegetable oils (sweet almond, macadamia, blackcurrant seed or jojoba oil); synthetic oils, such as perhydrosqualene, fatty alcohols, acids or esters (such as the benzoate of $C_{12}$–$C_{15}$ alcohols sold under the trade name "FINSOLV TN" by the company Finetex, octyl palmitate, isopropyl lanolate or triglycerides, including those of capric/caprylic acids), or oxyethylenated or oxypropylenated fatty ethers and esters; silicone oils (cyclomethicone, polydimethylsiloxanes or PDMS) or fluorinated oils, or polyalkylenes.

Mention may be made, as waxy compounds, of paraffin, carnauba wax, beeswax or hydrogenated castor oil.

Mention may be made, among organic solvents, of lower alcohols and polyols.

The thickeners can be selected in particular from crosslinked polyacrylic acids and modified or unmodified guar gums and celluloses, such as hydroxypropylated guar gum, methylhydroxyethylcellulose and hydroxypropylmethylcellulose.

Of course, a person skilled in the art will take care to choose the optional additional compound or compounds mentioned above (in particular the additional screening agents) and/or their amounts so that the advantageous properties intrinsically attached to the ternary combination in accordance with the invention are not, or not substantially, detrimentally affected by the envisaged addition or additions and so that the compositions of the invention exhibit good cosmetic properties.

The compositions according to the invention can be prepared according to techniques well known to a person skilled in the art, in particular those intended for the preparation of emulsions of oil-in-water or water-in-oil type.

This composition can in particular be provided in the form of a simple or complex emulsion (O/W, W/O, O/W/O or W/O/W), such as a cream or a milk, or in the form of a gel or of a cream gel, of a powder or of a solid stick and can optionally be packaged as an aerosol and be provided in the form of a foam or of a spray.

The compositions according to the invention are preferably provided in the form of an oil-in-water emulsion.

When it concerns an emulsion, the aqueous phase of the latter can comprise a non-ionic vesicular dispersion prepared according to known processes (Bangham, Standish and Watkins, J. Mol. Biol., 13, 238 (1965), FR 2,315,991 and FR 2,416,008, the disclosures of which are specifically incorporated by reference herein).

The cosmetic and/or dermatological composition of the invention can be used as composition for protecting the hair or human epidermis against ultraviolet rays, as anti-sun composition or as make-up product.

When the cosmetic composition according to the invention is used for protecting the human epidermis against UV rays or as anti-sun composition, it can be provided in the form of a suspension or dispersion in solvents or fatty substances, in the form of a non-ionic vesicular dispersion or in the form of an emulsion, preferably of oil-in-water type, such as a cream or a milk, or in the form of an ointment, gel, cream gel, solid stick, aerosol foam or spray.

When the cosmetic composition according to the invention is used for protecting the hair, it can be provided in the form of a hair lacquer, shampoo, lotion, gel, emulsion or non-ionic vesicular dispersion and can constitute, for example, a rinse-out composition, to be applied before or after shampooing, before or after dyeing or bleaching, or before, during or after a permanent-waving or hair-straightening operation, a styling or treating lotion or gel, a lotion or gel for blow-drying or hair setting, or a composition for the permanent-waving, straightening, dyeing or bleaching of the hair.

When the composition is used as a product for making up the eyelashes, eyebrows or skin, such as a cream for treatment of the epidermis, foundation, lipstick, eye shadow, blusher, mascara or eye liner, it can be provided in the anhydrous or aqueous, solid or pasty form, such as oil-in-water or water-in-oil emulsions, non-ionic vesicular dispersions, or suspensions.

By way of indication, for anti-sun formulations in accordance with the invention which exhibit a vehicle of oil-in-water emulsion type, the aqueous phase (comprising in particular the hydrophilic screening agents) preferably represents from 50 to 95% by weight, more preferably from 70 to 90% by weight, with respect to the whole formulation, the oily phase (comprising in particular the lipophilic screening agents) preferably from 5 to 50% by weight, more preferably from 10 to 30% by weight, with respect to the whole formulation, and the (co)emulsifier(s) preferably from 0.5 to 20% by weight, more preferably from 2 to 10% by weight, with respect to the whole formulation.

A concrete but in no way limiting example illustrating the invention will now be given.

TESTS

In the tests described hereinbelow, polyethyleneimine (PEI) with a molecular weight of 700 sold by the company Aldrich was used. The percentages shown in the definition of the formulae are percentages by weight of constituent with respect to the total weight of the formula.

Test 1: EX-VIVO Test of inhibition by polyethyleneimine of the photoperoxidation of 2-ethylhexyl p-methoxycinnamate induced by tocopherols A thin film of control composition (formula A: 2-ethylhexyl p-methoxycinnamate+vitamin E) was applied to a circular filter with an area of 17 cm$^2$ at the rate of approximately 3 mg/cm$^2$. The composition containing polyethyleneimine (product B: 2-ethylhexyl p-methoxycinnamate+vitamin E+PEI) was applied to a second filter. The filters were subsequently irradiated under 20 joules UV-A/cm$^2$ using a Biotronic 360 device.

The 2-ethylhexyl p-methoxycinnamate and its peroxides were extracted from the filters using 5 ml of ethanol, for the purpose of assaying the peroxides of the formula.

The results are expressed as inhibition of the peroxidation of 2-ethylhexyl p-methoxycinnamate:

$$\% \text{ inhibition} = \frac{\text{ROOH (formula A)} - \text{ROOH (formula B)}}{\text{ROOH (formula A)}} \times 100$$

ROOH represents the amount of 2-ethylhexyl p-methoxycinnamate peroxides in the composition (picomoles of peroxides as H$_2$O$_2$ equivalent per mg of product).

The compositions of the formulae A and B are given in the table hereinbelow:

| CTFA name | Formula A | Formula B |
|---|---|---|
| Cetyl alcohol | 5% | 5% |
| Glyceryl stearate | 3% | 3% |
| P.E.G. 50 stearate | 3% | 3% |
| Mineral oil | 18.5% | 18.5% |

-continued

| CTFA name | Formula A | Formula B |
|---|---|---|
| Caprylic/capric triglycerides | 3% | 3% |
| 2-Ethylhexyl p-methoxycinnamate | 0.5% | 0.5% |
| α-Tocopherol | 2% | 2% |
| Water | q.s. for 100% | q.s. for 100% |
| Polethyleneimine | 0% | 1% |

The following results were obtained:

| Formulae | Peroxides in pmol/mg |
|---|---|
| Formula A | 2214 |
| Formula B | 332 | i.e. 85% inhibition of the photoperoxidation of 2-ethylhexyl p-methoxycinnamate in the formula B with respect to the formula A.

TEST 2: Test of photostabilization of 2-ethylhexyl p-methoxycinnamate in the presence of 4-tert-butyl-4'-methoxydibenzoylmethane by polyethyleneimine under UV-A Films of anti-sun formula were prepared by manually spreading the formula at the rate of 2 mg/cm$^2$ over a depolished poly(methyl methacrylate) (PMMA) or depolished glass substrate.

The samples thus prepared were subsequently exposed for 2 H 30 or 4 H 30 to radiation from a Heraeus Sun-test (source: 1.8 kW Arc long Xenon) in a chamber, the temperature of which was adjusted to approximately from 35 to 40° C., in order to simulate natural UV irradiation.

This exposure corresponded to approximately 30 J/cm$^2$ UV-A (2 H 30) or 54 J/cm$^2$ UV-A (4 H 30).

After exposure, the UV screening agents were extracted with 63 ml of ethanol per sample.

The solutions obtained were analysed by spectrophotometry. The optical density of this solution at the $\lambda_{max}$ of the screening agent was measured.

The screening agents of a sample of control formula (same composition) applied to the depolished PMMA or depolished glass substrate but not subjected to UV irradiation were extracted and analysed in parallel according to the same protocol.

The level of residual screening agents after irradiation was given, for each of the screening agents of the formula, by the ratio of the optical density in the irradiated sample to its optical density in the non-irradiated sample (control sample).

The composition of the formulae tested is as follows:

| | A' | B' | C' | D' | E' |
|---|---|---|---|---|---|
| Polyethylene glycol stearate (40 EO) (sold by the company ICI under the trade name MYRJ 52) | 2 | 2 | 2 | 2 | 2 |
| Sorbitan Tristearate (sold by the company ICI under the trade name SPAN 65) | 0.9 | 0.9 | 0.9 | 0.9 | 0.9 |

-continued

|  | A' | B' | C' | D' | E' |
|---|---|---|---|---|---|
| Cetyl alcohol | 4 | 4 | 4 | 4 | 4 |
| Glyceryl stearate, pharmaceutical grade (Stéarinerie Dubois) | 3.3 | 3.3 | 3.3 | 3.3 | 3.3 |
| Benzoate of $C_{12}/C_{15}$ alcohols (sold by the company Witco under the trade name WITCONOL TN) | 10 | 10 | 10 | 10 | 10 |
| Liquid petrolatum | 5 | 5 | 5 | 5 | 5 |
| 4-tert-Butyl-4'-methoxydibenzoyl-methane | 2 | / | 2 | 2 | 2 |
| 2-Ethylhexyl p-methoxycinnamate | / | 5 | 5 | 5 | 5 |
| Polyethyleneimine | / | / | / | 4 | 8 |
| Hydrochloric acid | / | / | / | q.s. | q.s. |
| Glycerol | 6 | 6 | 6 | 6 | 6 |
| EDTA | 0.1 | 0.1 | 0.1 | 0.1 | 0.1 |
| Preservatives | q.s. | q.s. | q.s. | q.s | q.s. |
| Demineralized water q.s. for | 100 g | 100 g | 100 g | 100 g | 100 g |

Irradiation was carried out under 30 J/cm². The following result was obtained:

|  | % residual screening agent (4-tert-butyl-4'-methoxydibenzoylmethane), measured at 358 nm | % residual screening agent (2-ethylhexyl p-methoxycinnamate), measured at 310 nm |
|---|---|---|
| Formula A' | 8 ± 1 | — |
| Formula B' | — | 61 ± 5 |
| Formula C' | 11 ± 3 | 26 ± 3 |
| Formula D' | 19 ± 2 | 35 ± 2 |
| Formula E' | 27 ± 3 | 43 ± 3 |

We claim:

1. A cosmetic or dermatological composition comprising, in a cosmetically or dermatologically acceptable vehicle:

a) at least one cinnamic acid derivative of formula (I):

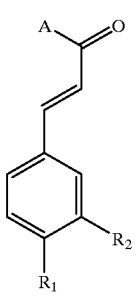

in which:

A is chosen from:
an $OR_3$ radical wherein $R_3$ is chosen from a hydrogen atom, a phytyl radical, a benzyl radical, a saturated or unsaturated, linear, branched or cyclic, $C_1$–$C_{18}$ alkyl chain, an alkali metal ion, an alkaline earth metal ion and an ammonium ion,
and
an $NHR_4$ radical wherein $R_4$ is chosen from a hydrogen atom, a phytyl radical, a benzyl radical, a saturated or unsaturated, linear, branched or cyclic, $C_1$–$C_{18}$ alkyl chain, $R_1$ is chosen from a hydrogen atom, a hydroxyl radical, a $C_1$–$C_6$ alkoxy radical, and a saturated or unsaturated, linear, branched or cyclic, $C_1$–$C_{18}$ alkyl chain;

$R_2$ is chosen from a hydrogen atom, a hydroxyl radical, and a $C_1$–$C_6$ alkoxy radical;

and b) at least one polyamino polymer chosen from:

(A) polyethyleneimines chosen from:

(i) polyethyleneimines;
(ii) alkylated derivatives of polyethyleneimines;
(iii) addition products of alkylcarboxylic acids with polyethyleneimines;
(iv) addition products of ketones and aldehydes with polyethyleneimines;
(v) addition products of isocyanates and isothiocyanates with polyethyleneimines;
(vi) addition products of alkylene oxide and poly(alkylene oxide) block polymers with polyethyleneimines;
(vii) quaternized derivatives of polyethyleneimines;
(viii) addition products of a silicone with polyethyleneimines;
(ix) a copolymer of dicarboxylic acid and polyethyleneimines;
(x) hyperbranched polyethyleneimines;

(B) polyvinylimidazoles;

(C) polyvinylpyridines;

(D) addition products of 1-vinylimidazole monomers of formula (I):

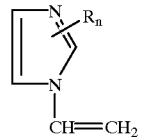

in which:

R radicals are independently chosen from a hydrogen atom and a saturated or unsaturated, linear or cyclic, $C_1$–$C_6$ alkyl radical n is an integer ranging from 1 to 3, with the polyethyleneimines (A)(I) to (A)(x);

(E) polymers based on amino acids containing a basic side chain; and (F) crosslinked derivatives of the polymers (A)(I) to (B), (C), (D) and (E).

2. A cosmetic or dermatological composition according to claim 1, wherein at least one of the following is true:

$R_1$ is methoxy; or
$R_2$ is methoxy.

3. A cosmetic or dermatological composition according to claim 1, wherein said composition further comprises at least one derivative of formula (II):

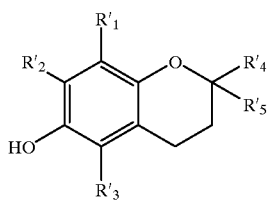

in which:

R'$_1$, R'$_2$ and R'$_3$ are independently chosen from a hydrogen atom, a hydroxyl radical and a C$_1$–C$_6$ alkyl radical, R'$_4$ is chosen from a hydrogen atom and a C$_1$–C$_6$ alkyl radical, and R'$_5$ is chosen from a hydrogen atom and a C$_1$–C$_{18}$ alkyl radical.

4. A cosmetic or dermatological composition according to claim 3, wherein at least one of the following is true:
R'$_1$ represents methyl;
R'$_2$ represents methyl;
R'$_3$ represents methyl; or
R'$_4$ represents methyl.

5. A cosmetic or dermatological composition according to claim 1, wherein said composition further comprises at least one dibenzoylmethane derivative of formula (III):

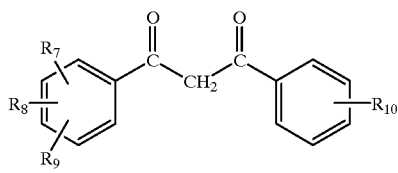

in which:

R$_7$, R$_8$, R$_9$ and R$_{10}$ are independently chosen from hydrogen, a hydroxyl radical, a linear or branched C$_1$–C$_8$ alkyl radical and a linear or branched C$_1$–C$_8$ alkoxy radical.

6. A cosmetic or dermatological composition according to claim 1, wherein said polyethyleneimines are chosen from polymers comprising at least 5% of tertiary amine functional groups.

7. A cosmetic or dermatological composition according to claim 6, wherein said polyethyleneimines are chosen from polymers comprising at least 10% of tertiary amine functional groups.

8. A cosmetic or dermatological composition according to claim 7, wherein said polyethyleneimines are chosen from polymers comprising at least 20% of tertiary amine functional groups.

9. A cosmetic or dermatological composition according to claim 1, wherein said at least one polyamino polymer is chosen from:
(A) (i) polyethyleneimines,
(ii) alkylated derivatives of polyethyleneimines;
(iii) addition products of alkylcarboxylic acids with polyethyleneimines;
(iv) addition products of ketones and aldehydes with polyethyleneimines;
(v) addition products of isocyanates and isothiocyanates with polyethyleneimines;
(vi) addition products of alkylene oxide and poly(alkylene oxide) block polymers with polyethyleneimines;
(vii) quaternized derivatives of polyethyleneimines;
(viii) addition products of a silicone with polyethyleneimines;
(ix) a copolymer of dicarboxylic acid and polyethyleneimines;
(x) hyperbranched polyethyleneimines; and
(B) polyvinylimidazoles.

10. A cosmetic or dermatological composition according to claim 9, wherein said at least one polyamino polymer is chosen from hyperbranched polyethyleneimines.

11. A cosmetic or dermatological composition according to claim 10, wherein said at least one polyamino polymer is chosen from hyperbranched polyethyleneimines comprising at least 5% of tertiary amines.

12. A cosmetic or dermatological composition according to claim 11, wherein said at least one polyamino polymer is chosen from hyperbranched polyethyleneimines comprising at least 10% of tertiary amines.

13. A cosmetic or dermatological composition according to claim 12, wherein said at least one polyamino polymer is chosen from hyperbranched polyethyleneimines comprising at least 20% of tertiary amines.

14. A cosmetic or dermatological composition according to claim 1, wherein said at least one polyamino polymer is present in an amount ranging from 0.1 to 10% by weight with respect to the total weight of said cosmetic or dermatological composition.

15. A cosmetic or dermatological composition according to claim 1, wherein said at least one polyamino polymer is present in an amount ranging from 0.25 to 5% by weight with respect to the total weight of said cosmetic or dermatological composition.

16. A cosmetic or dermatological composition according to claim 1, wherein said at least one cinnamic acid derivative is selected from 2-ethylhexyl p-methoxycinnamate, dihydroxycinnamic acid, chlorogenic acid, and carreoylquinic derivatives.

17. A cosmetic or dermatological composition according to claim 3, wherein said at least one cinnamic acid derivative is 2-ethylhexyl p-methoxycinnamate and said at least one derivative of formula (II) is a tocopherol derivative.

18. A cosmetic or dermatological composition according to claim 1, wherein said at least one cinnamic acid derivative is 2-ethylhexyl p-methoxycinnamate.

19. A cosmetic or dermatological composition according to claim 1, wherein said composition comprises said at least one cinnamic derivative, at least one derivative of formula (II):

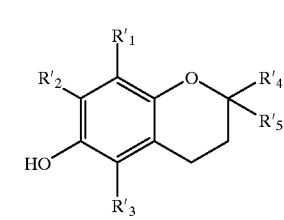

in which:

R'$_1$, R'$_2$ and R'$_3$ are independently chosen from a hydrogen atom, a hydroxyl radical and a C$_1$–C$_6$ alkyl radical, R'$_4$ is chosen from a hydrogen atom and a C$_1$–C$_6$ alkyl radical, and R'$_5$ is chosen from a hydrogen atom and a C$_1$–C$_{18}$ alkyl radical, and at least one dibenzoylmethane derivative of formula (III):

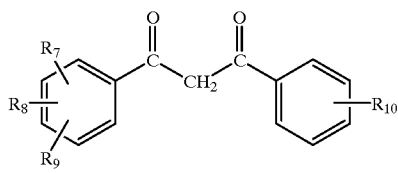

(III)

in which:
$R_7$, $R_8$, $R_9$ and $R_{10}$ are independently chosen from hydrogen a hydroxyl radical, a linear or branched $C_1$–$C_8$ alkyl radical and a linear or branched $C_1$–$C_8$ alkoxy radical.

20. A cosmetic or dermatological composition according to claim 1, wherein said at least one cinnamic acid derivative is present in an amount ranging from 0.1% to 10% by weight with respect to the total weight of said cosmetic or dermatological composition.

21. A cosmetic or dermatological composition according to claim 17, wherein said at least one cinnamic acid derivative is present in an amount ranging from 0.5% to 5% by weight with respect to the total weight of said cosmetic or dermatological composition.

22. A cosmetic or dermatological composition according to claim 3, wherein said at least one derivative of formula (II) is tocopherol.

23. A cosmetic or dermatological composition according to claim 3, wherein said at least one derivative of formula (II) is a mixture of natural tocopherols.

24. A cosmetic or dermatological composition according to claim 3, wherein said at least one derivative of formula (II) is present in the composition in an amount ranging from 0.5% to 20% by weight with respect to the total weight of said cosmetic dermatological composition.

25. A cosmetic or dermatological composition according to claim 21, wherein said derivative of formula (II) is present in the composition in an amount ranging from 1% to 10% by weight with respect to the total weight of said cosmetic dermatological composition.

26. A cosmetic or dermatological composition according to claim 5, wherein said at least one dibenzoylmethane derivative of formula (III) is chosen from:
  2-methyldibenzoylmethane,
  4-methyldibenzoylmethane,
  4-isopropyldibenzoylmethane,
  4-tert-butyldibenzoylmethane,
  2,4-dimethyldibenzoylmethane,
  2,5-dimethyldibenzoylmethane,
  4,4'-diisopropyldibenzoylmethane,
  4-tert-butyl-4'-methoxydibenzoylmethane,
  2-methyl-5-isopropyl-4'-methoxydibenzoylmethane,
  2-methyl-5-tert-butyl-4'-methoxydibenzoylmethane,
  2,4-dimethyl-4'-methoxydibenzoylmethane,
  2,6-dimethyl-4-tert-butyl-4'-methoxydibenzoylmethane, and
  4,4'-dimethoxydibenzoylmethane.

27. A cosmetic or dermatological composition according to claim 23, wherein said at least one dibenzoylmethane derivative of formula (III) is 4-tert-butyl-4'-methoxydibenzoyl-methane corresponding to the formula:

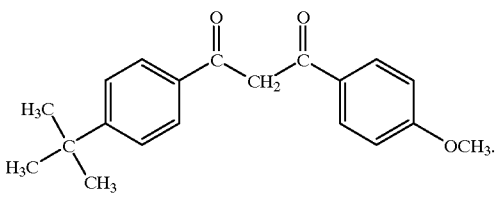

28. A cosmetic or dermatological composition according to claim 23, wherein said at least one dibenzoylmethane derivative of formula (III) is 4-isopropyldibenzoylmethane corresponding to the formula:

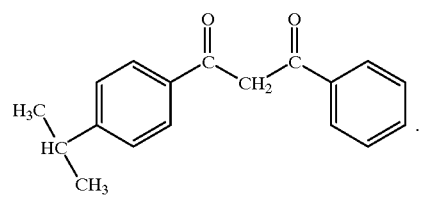

29. A cosmetic or dermatological composition according to claim 5, wherein said at least one dibenzoylmethane derivative of formula (III) is present in the composition in an amount ranging from 0.2% to 15% by weight with respect to the total weight of said cosmetic or dermatological composition.

30. A cosmetic or dermatological composition according to claim 26, wherein said at least one dibenzoylmethane derivative of formula (III) is present in the composition in an amount ranging from 0.2% to 10% by weight with respect to the total weight of said cosmetic or dermatological composition.

31. A cosmetic or dermatological composition according to claim 1, wherein said composition is in the form of a simple or complex emulsion, a gel, a cream gel, a powder, a foam, a spray or a solid.

32. A cosmetic or dermatological composition according to claim 28, wherein said composition is in the form of an oil-in-water emulsion.

33. A cosmetic or dermatological composition according to claim 1, wherein said composition further comprises at least one additional sunscreen agent.

34. A cosmetic or dermatological composition according to claim 1, wherein said composition further comprises at least one artificial tanning agent or self-tanning agent.

35. A cosmetic or dermatological composition according to claim 1, wherein said composition further comprises at least one pigment.

36. A cosmetic or dermatological composition according to claim 1, wherein said composition further comprises at least one conventional cosmetic adjuvant.

37. A cosmetic or dermatological composition according to claim 1, wherein the at least one polyamino polymer is linear, dendrimitic, or hyperbranched.

38. A cosmetic or dermatological composition according to claim 37, wherein the at least one polyamino polymer is a hyperbranched polyethyleneimine.

* * * * *